United States Patent
Seo et al.

(10) Patent No.: US 11,698,365 B2
(45) Date of Patent: Jul. 11, 2023

(54) APPARATUS AND METHOD FOR DETECTING ALCOHOL CONTENT OF VEHICLE OCCUPANT'S BREATH

(71) Applicants: Hyundai Motor Company, Seoul (KR); Kia Motors Corporation, Seoul (KR)

(72) Inventors: Sang Kyung Seo, Seoul (KR); Eung Hwan Kim, Seoul (KR); Gyun Ha Kim, Incheon (KR); Dae Yun An, Gyeonggi-do (KR)

(73) Assignees: Hyundai Motor Company, Seoul (KR); Kia Motors Corporation, Seoul (KR)

( * ) Notice: Subject to any disclaimer, the term of this patent is extended or adjusted under 35 U.S.C. 154(b) by 298 days.

(21) Appl. No.: 17/035,048

(22) Filed: Sep. 28, 2020

(65) Prior Publication Data
US 2022/0003747 A1  Jan. 6, 2022

(30) Foreign Application Priority Data
Jul. 6, 2020 (KR) .................... 10-2020-0082866

(51) Int. Cl.
*G01N 33/497* (2006.01)
*B60K 28/06* (2006.01)

(52) U.S. Cl.
CPC ....... *G01N 33/4972* (2013.01); *B60K 28/063* (2013.01)

(58) Field of Classification Search
USPC .......................................... 73/23.3
See application file for complete search history.

(56) References Cited

U.S. PATENT DOCUMENTS

| | | | | |
|---|---|---|---|---|
| 2009/0205407 A1* | 8/2009 | Marhefka | .......... | G01N 33/4972 73/23.3 |
| 2010/0043524 A1* | 2/2010 | Takata | ............... | G01N 33/4972 73/23.3 |
| 2011/0102182 A1* | 5/2011 | Ohya | .................. | G01N 33/497 340/576 |
| 2012/0198910 A1* | 8/2012 | Lo | ...................... | G01N 33/4972 73/23.3 |
| 2014/0076022 A1* | 3/2014 | Ohlsson | ............. | G01N 33/4972 73/23.3 |

(Continued)

*Primary Examiner* — Peter J Macchiarolo
*Assistant Examiner* — Mohammed E Keramet-Amircolai
(74) *Attorney, Agent, or Firm* — Fox Rothschild LLP

(57) ABSTRACT

An apparatus for detecting an alcohol component of a driver's breath includes an inlet that absorbs a driver's exhalation and a passenger's exhalation, respectively, a sensor that detects an alcohol component in the driver's exhalation or the passenger's exhalation, a driver valve controlled to be opened or closed to allow the driver's exhalation to be introduced into the sensor and a passenger valve controlled to be opened or closed to allow the passenger's exhalation to be introduced into the sensor, and a controller that determines whether a passenger is on board a vehicle and controls the driver valve and the passenger valve to be open or closed based on a determination result. Therefore, the driver's breath is distinguished from the passenger's breath and the influence of the passenger is removed to detect the alcohol component in the driver's breath, thereby accurately determining the driver's drinking state.

20 Claims, 7 Drawing Sheets

(56) References Cited

U.S. PATENT DOCUMENTS

| | | | |
|---|---|---|---|
| 2014/0165698 A1* | 6/2014 | Mochizuki | G01N 33/4972 73/23.3 |
| 2014/0311214 A1* | 10/2014 | Wolf, Jr. | G01N 33/4972 73/23.3 |
| 2014/0366609 A1* | 12/2014 | Beck | G01N 33/497 73/23.3 |
| 2017/0274768 A1* | 9/2017 | Hök | G01N 33/0067 |
| 2018/0074030 A1* | 3/2018 | DeVries | G01N 33/0006 |
| 2019/0113502 A1* | 4/2019 | Ruland | G01N 33/4972 |
| 2020/0103394 A1* | 4/2020 | Dennis | G01N 33/497 |
| 2021/0101482 A1* | 4/2021 | Seo | B60K 28/063 |

* cited by examiner

APPARATUS AND METHOD FOR DETECTING ALCOHOL CONTENT OF VEHICLE OCCUPANT'S BREATH

CROSS-REFERENCE TO RELATED APPLICATION

This application claims under 35 U.S.C. § 119(a) the benefit of Korean Patent Application No. 10-2020-0082866, filed in the Korean Intellectual Property Office on Jul. 6, 2020, the entire contents of which are incorporated herein by reference.

BACKGROUND

(a) Technical Field

The present disclosure relates to an apparatus for detecting an alcohol content of a vehicle occupant's breath and a method thereof.

(b) Description of the Related Art

In a conventional alcohol detection apparatus, a driver's seat in a vehicle is provided with an inlet for detecting an alcohol component contained in a driver's breath to determine whether or not the driver in a vehicle is above the legal limit, and thus considered drunk. However, the inlet provided in the driver's seat detects not only the driver's breathing, but also a passenger's breathing next to the driver, thereby making it difficult to accurately determine the driver's drinking state.

SUMMARY

An aspect of the present disclosure provides an apparatus for detecting an alcohol content (component) that distinguishes a driver's breath from a passenger's breath in a vehicle to accurately determine a driver's drinking state, and a method thereof.

The technical problems to be solved by the present inventive concept are not limited to the aforementioned problems, and any other technical problems not mentioned herein will be clearly understood from the following description by those skilled in the art to which the present disclosure pertains.

According to an aspect of the present disclosure, an apparatus for detecting an alcohol component includes an inlet that absorbs a driver's exhalation and a passenger's exhalation, respectively, a sensor that detects an alcohol component in at least one of the driver's exhalation or the passenger's exhalation, a driver valve controlled to be opened or closed to allow the driver's exhalation to be introduced into the sensor and a passenger valve controlled to be opened or closed to allow the passenger's exhalation to be introduced into the sensor, and a controller that determines whether a passenger is on board (i.e., present in) a vehicle and controls the driver valve and the passenger valve to be open or closed based on a determination result.

The controller may control the driver valve and the passenger valve to be opened or closed to allow the driver's exhalation and the passenger's exhalation to be alternately introduced into the sensor when it is determined that the passenger is on board the vehicle based on the determination result.

The controller may control the driver valve to be opened and controls the passenger valve to be closed for a predetermined first time, to introduce the driver's exhalation into the sensor when the passenger is on board the vehicle, and then the controller may control the driver valve to be closed and controls the passenger valve to be opened for the first time, to introduce the passenger's exhalation into the sensor, thereby alternately introducing the driver's exhalation and the passenger's exhalation alternately into the sensor.

The controller may determine whether either the driver's exhalation or the passenger's exhalation flowed into the sensor based on the predetermined first time.

The controller may control the driver valve to be opened and controls the passenger valve to be closed, to introduce the driver's exhalation into the sensor and not to introduce the passenger's exhalation into the sensor when it is determined that the passenger is not on board the vehicle based on the determination result Before starting the engine, the controller may determine whether the alcohol component is detected in the driver's exhalation and the passenger's exhalation which are alternately introduced into the sensor and the controller may determine the engine is capable of being started when the alcohol component is not detected in the driver's exhalation.

After starting the engine, the controller may determine whether the alcohol component is detected in the driver's exhalation and the passenger's exhalation alternately introduced into the sensor while driving and the controller may determine the driving is maintained when the alcohol component is not detected in the driver's exhalation.

The controller may determine whether the alcohol component is detected in the passenger's exhalation when the alcohol component is detected in the driver's exhalation while driving and the controller may output a warning and controls to stop driving when the alcohol component is not detected in the passenger's exhalation.

The controller may output a ventilation request message of a vehicle interior and may control to redetect the alcohol component in the driver's exhalation and the passenger's exhalation when the alcohol component is detected in the passenger's exhalation.

The driver valve and the passenger valve may each include a solenoid valve, respectively.

According to an aspect of the present disclosure, a method of detecting an alcohol component includes determining whether a passenger is on board (i.e., present in) a vehicle, controlling a driver valve and a passenger valve to be opened or closed based on a determination result of the passenger's boarding, and detecting an alcohol component in at least one of a driver's exhalation or a passenger's exhalation introduced into the sensor in response to opening or closing of the driver valve and the passenger valve.

The driver valve and the passenger valve may be controlled to be opened or closed when it is determined that the passenger is on board the vehicle based on the determination result, thereby allowing the driver's exhalation and the passenger's exhalation to alternately be introduced into the sensor.

The driver valve may be controlled to be opened and the passenger valve may be controlled to be closed for a predetermined first time when the passenger is on board the vehicle, thereby allowing the driver's exhalation to be introduced into the sensor, and then the driver valve may be controlled to be closed and the passenger valve may be controlled to be opened for the predetermined first time, thereby allowing the passenger's exhalation to be introduced into the sensor, thereby allowing the driver's exhalation and the passenger's exhalation to alternately be introduced into the sensor.

It may be determined whether either the driver's exhalation or the passenger's exhalation is introduced into the sensor based on the preset first time.

The driver valve may be controlled to be opened and the passenger valve may be controlled to be closed when the passenger is not on board the vehicle based on the determination result, thereby allowing the driver's exhalation to be introduced into the sensor and to allow the passenger's exhalation not to be introduced into the sensor.

Before starting the engine, it may be determined whether the alcohol component is detected in the driver's exhalation and the passenger's exhalation alternately introduced into the sensor and it may be determined the engine is capable of being started when the alcohol component is not detected in the driver's exhalation.

After starting the engine, it may be determined whether the alcohol component is detected in the driver's exhalation and the passenger's exhalation alternately introduced into the sensor while driving and it may be controlled to maintain driving when the alcohol component is not detected in the driver's exhalation.

It may be determined whether the alcohol component is detected in the passenger's exhalation when the alcohol component is detected in the driver's exhalation while driving and a waning may be output and it may be controlled to stop driving when the alcohol component is not detected in the passenger's exhalation.

A vehicle interior ventilation request message may be output and it may be controlled to redetect the alcohol component in the driver's exhalation and the passenger's exhalation when the alcohol component is detected in the passenger's exhalation.

The driver valve and the passenger valve may each include a solenoid valve, respectively.

BRIEF DESCRIPTION OF THE DRAWINGS

The above and other objects, features and advantages of the present disclosure will be more apparent from the following detailed description taken in conjunction with the accompanying drawings.

DETAILED DESCRIPTION

Figure 1:
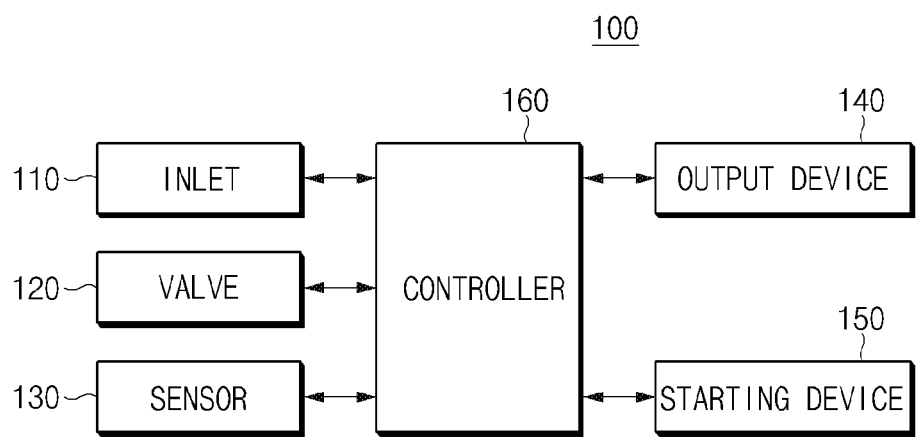
FIG. 1 is a diagram illustrating a configuration of an apparatus for detecting an alcohol component of a vehicle occupant's breath according to an embodiment of the present disclosure.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g. fuels derived from resources other than petroleum). As referred to herein, a hybrid vehicle is a vehicle that has two or more sources of power, for example both gasoline-powered and electric-powered vehicles.

The terminology used herein is for the purpose of describing particular embodiments only and is not intended to be limiting of the disclosure. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Throughout the specification, unless explicitly described to the contrary, the word "comprise" and variations such as "comprises" or "comprising" will be understood to imply the inclusion of stated elements but not the exclusion of any other elements. In addition, the terms "unif" "-er", "-or", and "module" described in the specification mean units for processing at least one function and operation, and can be implemented by hardware components or software components and combinations thereof.

Further, the control logic of the present disclosure may be embodied as non-transitory computer readable media on a computer readable medium containing executable program instructions executed by a processor, controller or the like. Examples of computer readable media include, but are not limited to, ROM, RAM, compact disc (CD)-ROMs, magnetic tapes, floppy disks, flash drives, smart cards and optical data storage devices. The computer readable medium can also be distributed in network coupled computer systems so that the computer readable media is stored and executed in a distributed fashion, e.g., by a telematics server or a Controller Area Network (CAN).

Hereinafter, some embodiments of the present disclosure will be described in detail with reference to the exemplary drawings. In adding the reference numerals to the components of each drawing, it should be noted that the identical or equivalent component is designated by the identical numeral even when they are displayed on other drawings. Further, in describing the embodiment of the present disclosure, a detailed description of well-known features or functions will be ruled out in order not to unnecessarily obscure the gist of the present disclosure.

In describing the components of the embodiment according to the present disclosure, terms such as first, second, "A", "B", (a), (b), and the like may be used. These terms are merely intended to distinguish one component from another component, and the terms do not limit the nature, sequence or order of the constituent components. Unless otherwise defined, all terms used herein, including technical or scientific terms, have the same meanings as those generally understood by those skilled in the art to which the present disclosure pertains. Such terms as those defined in a generally used dictionary are to be interpreted as having meanings equal to the contextual meanings in the relevant field of art, and are not to be interpreted as having ideal or excessively formal meanings unless clearly defined as having such in the present application.

FIG. 1 is a diagram illustrating a configuration of an apparatus for detecting an alcohol component of a vehicle occupant's breath according to an embodiment of the present disclosure.

As illustrated in FIG. 1, an apparatus for detecting an alcohol component 100 may include an inlet 110, a valve 120, a sensor 130, an output device 140, and a starting device 150.

The inlet 110 may absorb exhalation of a driver and exhalation of a passenger, respectively. To this end, the inlet 110 may be provided on a position that is capable of easily absorbing the driver's exhalation, e.g., one side of a steering wheel and a position that is capable of easily absorbing the passenger's exhalation, e.g., one side of a dashboard of the passenger's seat.

The valve 120 may include a driver valve which is controlled to open or close to allow the driver's exhalation to flow into the sensor 130 and a passenger valve which is controlled to open or close to allow the passenger's exhalation to flow into the sensor 130. Here, the driver valve and the passenger valve may each include a solenoid valve controlled by a controller 160. The valve 120 may be provided at a position where a snorkel (driver's exhalation passage), to which the inlet 110 absorbing the driver's exhalation is connected, and a snorkel (passenger's exhalation passage), to which the inlet 110 absorbing the passenger's exhalation is connected, intersect each other.

The sensor 130 may detect an alcohol component in at least one of the driver's exhalation or the passenger's exhalation. In this case, the sensor 130 may include an alcohol sensor. Here, the alcohol component may include an alcohol component having an alcohol concentration above a threshold determined to be a drinking state, but is not limited thereto, and may also include an alcohol component having an alcohol concentration below the threshold.

In addition, the sensor 130 may be provided in the driver's seat and the passenger's seat to detect driver boarding and passenger boarding. In this case, the sensor 130 may be implemented as a seat sensor.

The output device 140 may output a determination result of the controller 160. To this end, the output device 140 may include a cluster display device and an audio video navigation (AVN) display device, which are capable of outputting an image, and a speaker capable of outputting sound.

The starting device 150 may refer to an engine starting device of a vehicle, and may cause an engine to be driven or halted based on the determination result of the controller 160. According to an embodiment, in the determination result of the controller 160, when it is determined that the alcohol component is not detected in the driver's exhalation, the engine may be driven by determining to be able to start, and when it is determined that the alcohol component is detected in the driver's exhalation, the engine may be prevented from being driven.

The controller 160 may be implemented by various processing devices such as a microprocessor equipped with a semiconductor chip capable of performing calculation or execution of various instructions. The controller 160 may control operation of the apparatus for detecting the alcohol component according to an embodiment of the present disclosure. Specifically, the controller 160 may determine whether the passenger is on board a vehicle and control the driver valve and the passenger valve to be opened or closed based on the determination result.

In particular, in the determination result, when it is determined that the passenger is on board the vehicle, the controller 160 may control the driver valve and passenger valve to be opened or closed and allow the driver's exhalation and the passenger's exhalation to alternately flow into the sensor. A detailed description will be given with reference to FIGS. 2 and 3.

Figure 2:
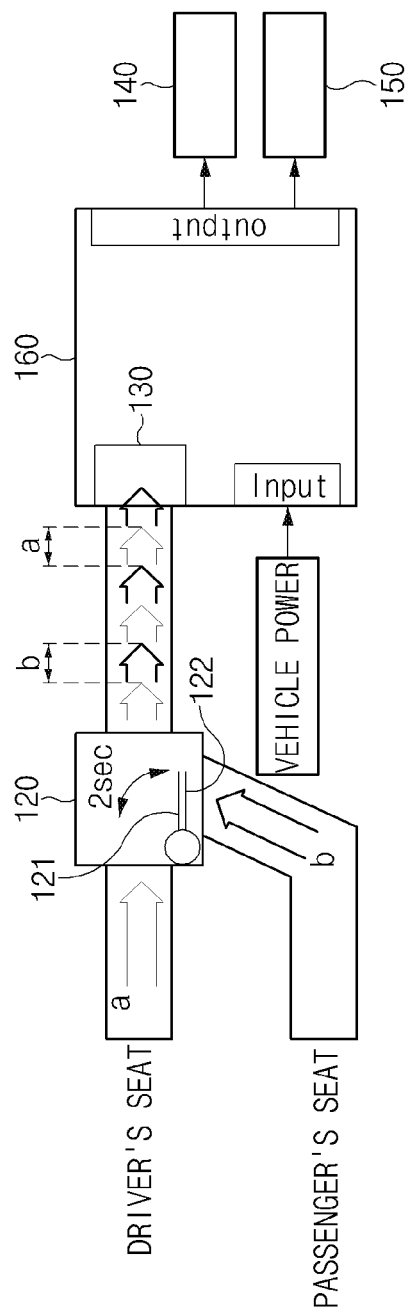
FIG. 2 is a view illustrating a state in which a valve of a driver's seat is opened according to an embodiment of the present disclosure.
Figure 3:
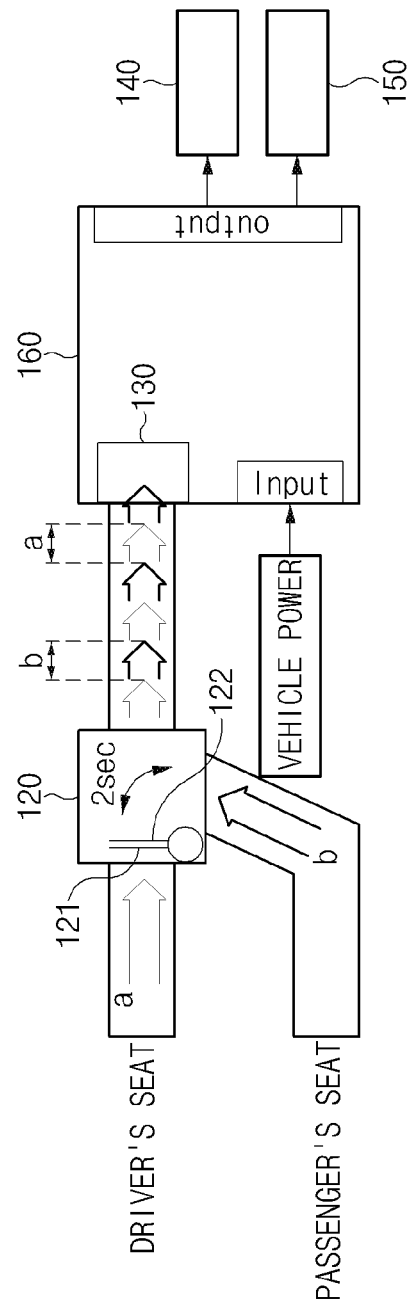
FIG. 3 is a view illustrating a state in which a valve of a passenger's seat is opened according to an embodiment of the present disclosure.

FIG. 2 is a view illustrating a state in which a valve of a driver's seat is opened according to an embodiment of the present disclosure, and FIG. 3 is a view illustrating a state in which a valve of a passenger's seat is opened according to an embodiment of the present disclosure.

As illustrated in FIG. 2, the controller 160 may control a driver valve 121 to be opened for a first time after a driver's exhalation "a" is absorbed through the inlet 110 and may control a passenger valve 122 to be closed, thereby allowing the driver's exhalation "a" to be introduced into the sensor 130. Here, the first time may include a time of 2 seconds to 5 seconds according to an embodiment.

In addition, as illustrated in FIG. 3, the controller 160 controls the driver valve 121 to be closed for the first time after the driver's exhalation "a" flows in for the first time and may control the passenger valve 122 to be opened, thereby allowing the passenger's exhalation "b" to be introduced into the sensor 130.

Therefore, because the driver's exhalation "a" and the passenger's exhalation "b" may be alternately introduced at an interval of the first time, the controller 160 may determine whether the exhalation sensed by the sensor 130 for a specific time is the driver's or a passenger's based on the first time. Here, it is preferable that the specific time is understood as a time at which information sufficient to distinguish the driver's exhalation from the passenger's exhalation is obtained.

Thus, the sensor 130 may distinguish the driver's exhalation and the passenger's exhalation and detect the alcohol component of each exhalation to allow the controller 160 to accurately detect the alcohol component in the driver's exhalation. Also, the controller 160 may output the determination result through the output device 140 or control the starting device 150 based on the determination result.

Meanwhile, when it is determined that the passenger is not on board (i.e., present in) the vehicle, the controller 160 may control the driver valve 121 to be opened and control the passenger valve 122 to be closed as illustrated in FIG. 2 to allow the driver's exhalation to be introduced into the sensor 130 and to allow the passenger's exhalation not to be introduced into the sensor 130. Therefore, when the passenger is not on board the vehicle, the controller 160 may fundamentally block the passenger's exhalation, to allow the alcohol component in the driver's exhalation to be accurately detected.

Before starting the engine, the controller 160 may determine whether the alcohol component is detected in the driver's exhalation and the passenger's exhalation alternately introduced into the sensor 130.

When the alcohol component is not detected in the driver's exhalation, the controller 160 may determine that the engine is capable of being started. On the other hand, when the alcohol component is detected in the driver's exhalation, the controller 160 may not start the engine, but may allow the driver's exhalation and the passenger's exhalation to be introduced again.

When it is determined that the engine is capable of being started, the controller 160 may introduce the driver's exhalation and the passenger's exhalation in the driving state after starting the engine. The controller 160 may determine whether the alcohol component in the driver's exhalation and the passenger's exhalation absorbed while driving are detected.

When the alcohol component in the driver's exhalation is not detected in the driving state, the controller 160 may control to maintain driving. Meanwhile, when the alcohol component in the driver's exhalation is detected in the driving state, the controller 160 may determine whether the alcohol component in the passenger's exhalation is detected.

When it is determined that the alcohol component is not detected in the passenger's exhalation, the controller 160 may output a warning message and control to stop driving. On the other hand, when it is determined that the alcohol component is detected in the passenger's exhalation, the controller 160 may output a guide message requesting indoor ventilation of the vehicle, and control to reabsorb the driver's exhalation and the passenger's exhalation in the driving state.

Figure 4:
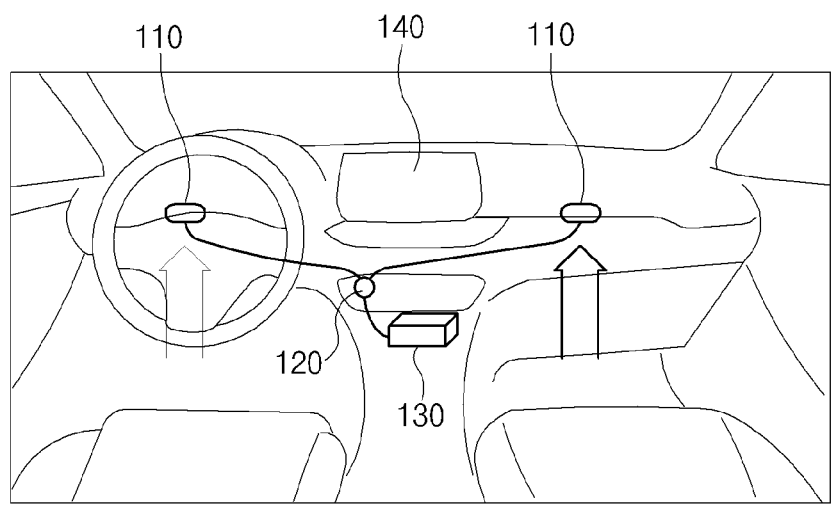
FIG. 4 is a view schematically illustrating an apparatus for detecting an alcohol component mounted in a vehicle according to an embodiment of the present disclosure.

FIG. 4 is a view schematically illustrating an apparatus for detecting an alcohol component mounted in a vehicle according to an embodiment of the present disclosure.

As illustrated in FIG. 4, the apparatus for detecting the alcohol component 100 of the present disclosure may include the inlet 110 which absorbs the driver's exhalation and is provided on one side of the steering wheel, and the inlet 110 which absorbs the passenger's exhalation and is provided on one side of the dashboard.

In addition, the valve 120 may be provided at a position where a snorkel (driver's exhalation passage), to which the inlet 110 absorbing the driver's exhalation is connected, and a snorkel (passenger's exhalation passage), to which the inlet 110 absorbing the passenger's exhalation is connected, intersect each other, thereby be controlled to be opened or closed based on control of the controller 160.

The sensor 130 may detect the alcohol component in the driver's exhalation and the passenger's exhalation and may detect whether the passenger is on board the vehicle.

The output device 140 may output the determination result of the controller 160. To this end, the output device 140 may include a cluster display device and an AVN display device, which are capable of outputting an image, and a speaker capable of outputting sound.

Figure 5:
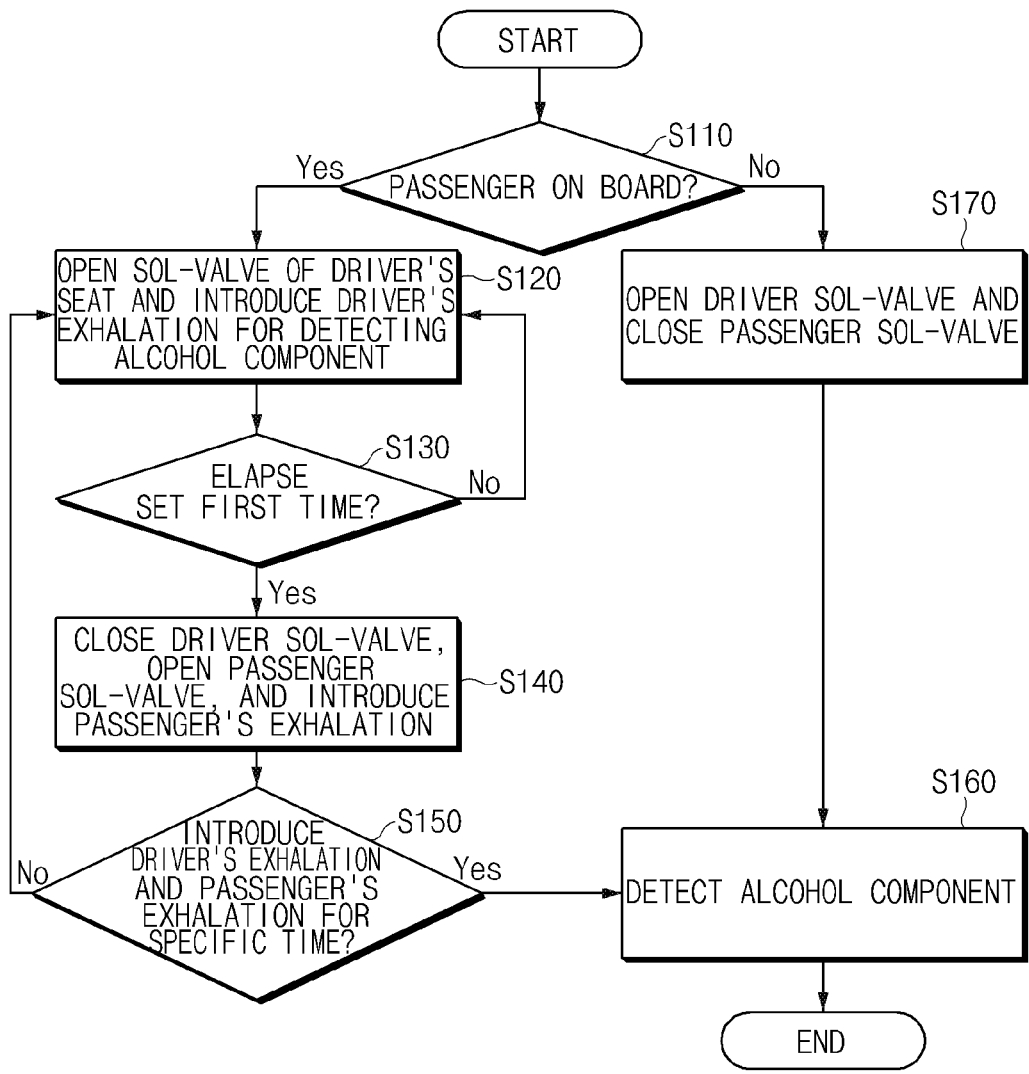
FIG. 5 is a view illustrating a method for detecting an alcohol component according to an embodiment of the present disclosure.

FIG. 5 is a view illustrating a method for detecting an alcohol component according to an embodiment of the present disclosure.

As illustrated in FIG. 5, the controller 160 determines whether the passenger is on board in the vehicle based on the information detected by the sensor 130 in S110. In S110, when it is determined that the passenger is on board "Y" the vehicle, the controller 160 may control the driver valve and the passenger valve to be opened or closed to allow the driver's exhalation and the passenger's exhalation to alternately be introduced into the sensor.

Specifically, after the driver's exhalation is absorbed through the inlet 110, the controller 160 may control the driver valve 121 to be opened and control the passenger valve 122 to be closed for the first time, thereby allowing the driver's exhalation "a" to be introduced into the sensor 130 in S120. In S120, the first time may include a time of 2 seconds to 5 seconds according to an embodiment.

After the driver's exhalation flows for the first time, the controller 160 may control the driver valve 121 to be closed for the first time, and control the passenger valve 122 to be opened, thereby allowing the passenger's exhalation to flow into the sensor 130 in S140.

The controller 160 determines whether the driver's exhalation and the passenger's exhalation are introduced for a specific time in S150. Here, the specific time may be a time at which information sufficient to distinguish the driver's exhalation from the passenger's exhalation is obtained. When the controller 160 determines that the driver's exhalation and the passenger's exhalation are introduced for the specific time "Y", the controller 160 may determine whether the exhalation sensed by the sensor 130 is the driver's or passenger's based on the first time and the controller 160 detects the alcohol component in the exhalation (driver's exhalation and passenger's exhalation) alternately introduced at the interval of the first time in S160.

That is, the controller 160 may allow the sensor 130 to distinguish the driver's exhalation from the passenger's exhalation and to detect the alcohol component of each exhalation, thereby accurately detecting the alcohol component in the driver's exhalation. In addition, the controller 160 may output the determination result through the output device 140 or control the starting device 150 based on the determination result.

Meanwhile, in S110, when the controller 160 determines that the passenger is not on board "N" the vehicle, the controller 160 may control the driver valve 121 to be opened and control the passenger valve 122 to be closed in S170, to introduce only the driver's exhalation into the sensor 130 and not to introduce the passenger's exhalation into the sensor 130. Thereafter, the alcohol component is detected in the exhalation (driver's exhalation) sensed by the sensor 130 in S160. Therefore, when the passenger is not on board the vehicle, the controller 160 may fundamentally block the passenger's exhalation, to allow the alcohol component in the driver's exhalation to be accurately detected.

Figure 6:
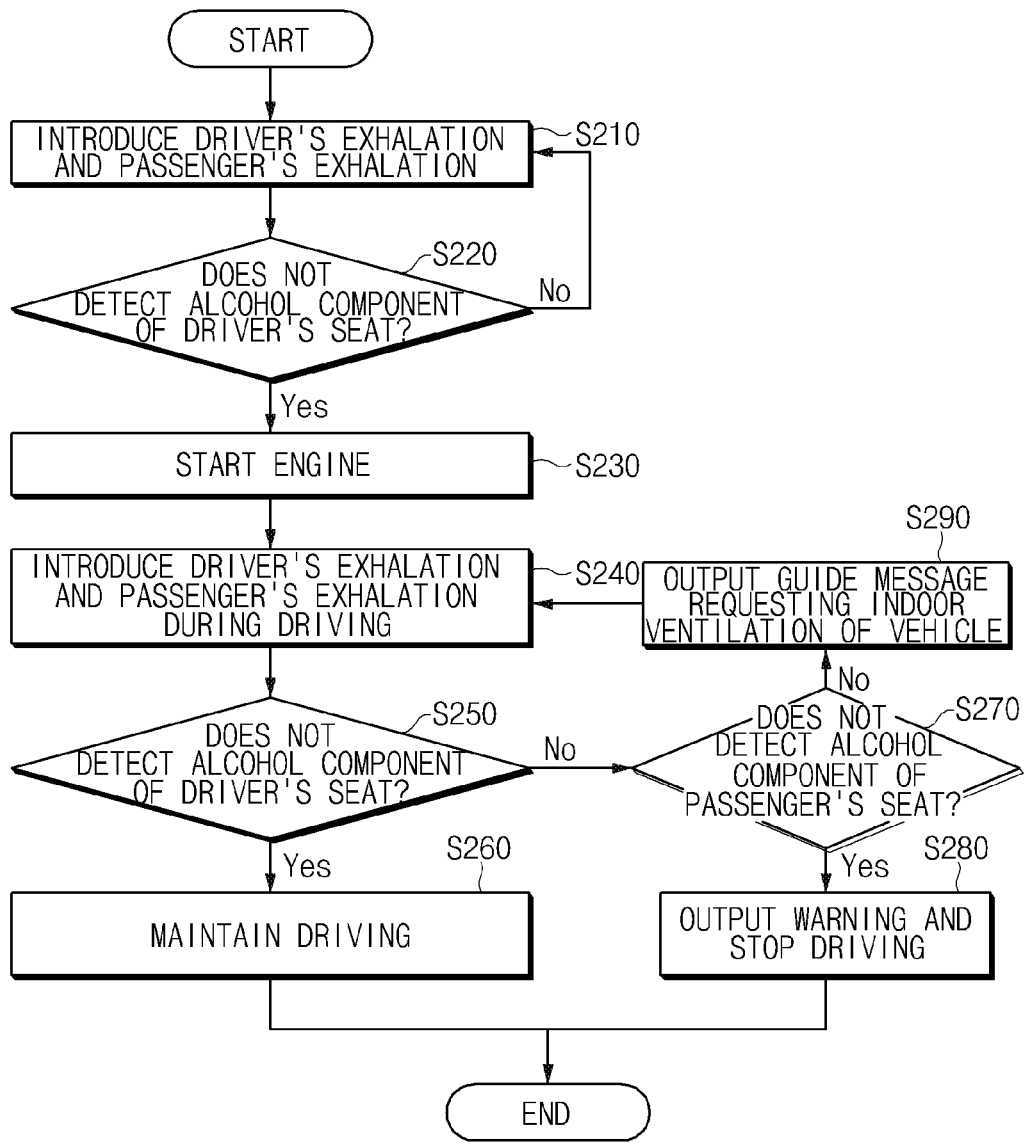
FIG. 6 is a view illustrating a method for detecting an alcohol component according to another embodiment of the present disclosure.

FIG. 6 is a view illustrating a method for detecting an alcohol component according to another embodiment of the present disclosure.

As illustrated in FIG. 6, the controller 160 determines whether the passenger is on board the vehicle based on the information sensed by the sensor 130, and when the passenger is on board the vehicle, the driver's exhalation and the passenger's exhalation are introduced in S210. A more detailed description of S210 will be given with reference to S120 to S150 in FIG. 5.

Before starting the engine, the controller 160 may determine whether the alcohol component is not detected in the driver's exhalation and the passenger's exhalation, which are alternately introduced into the sensor 130 in S220.

In S220, when the alcohol component is not detected in the driver's exhalation "Y", the controller 160 may determine that the engine may be started in S230. Meanwhile, in S220, when the alcohol component is detected in the driver's exhalation "N", the controller 160 may introduce the driver's exhalation and the passenger's exhalation again in S210 while the engine is not started.

When it is determined that the engine is started, the controller 160 may allow the driver's exhalation and the passenger's exhalation to be introduced in the driving state after starting the engine in S240. The controller 160 may determine whether the alcohol component is detected in the driver's exhalation and the passenger's exhalation absorbed while driving in S250.

When the alcohol component in the driver's exhalation is not detected "Y" in the driving state in S250, the controller 160 may control to maintain driving in S260. Meanwhile, when the alcohol component in the driver's exhalation is detected in the driving state in S250, the controller 160 may determine whether the alcohol component in the passenger's exhalation is not detected in S270.

When the controller 160 determines that the alcohol component in the passenger's exhalation is not detected "Y" in S270, the controller 160 may output a waning message and control stop driving in S280. On the other hand, when it is determined that the alcohol component is detected in the passenger's exhalation "Y" in S270, the controller 160 may output a guide message requesting indoor ventilation of the vehicle in S290 and may control the driver's exhalation and the passenger's exhalation to be reabsorbed in the driving state in S240.

Figure 7:
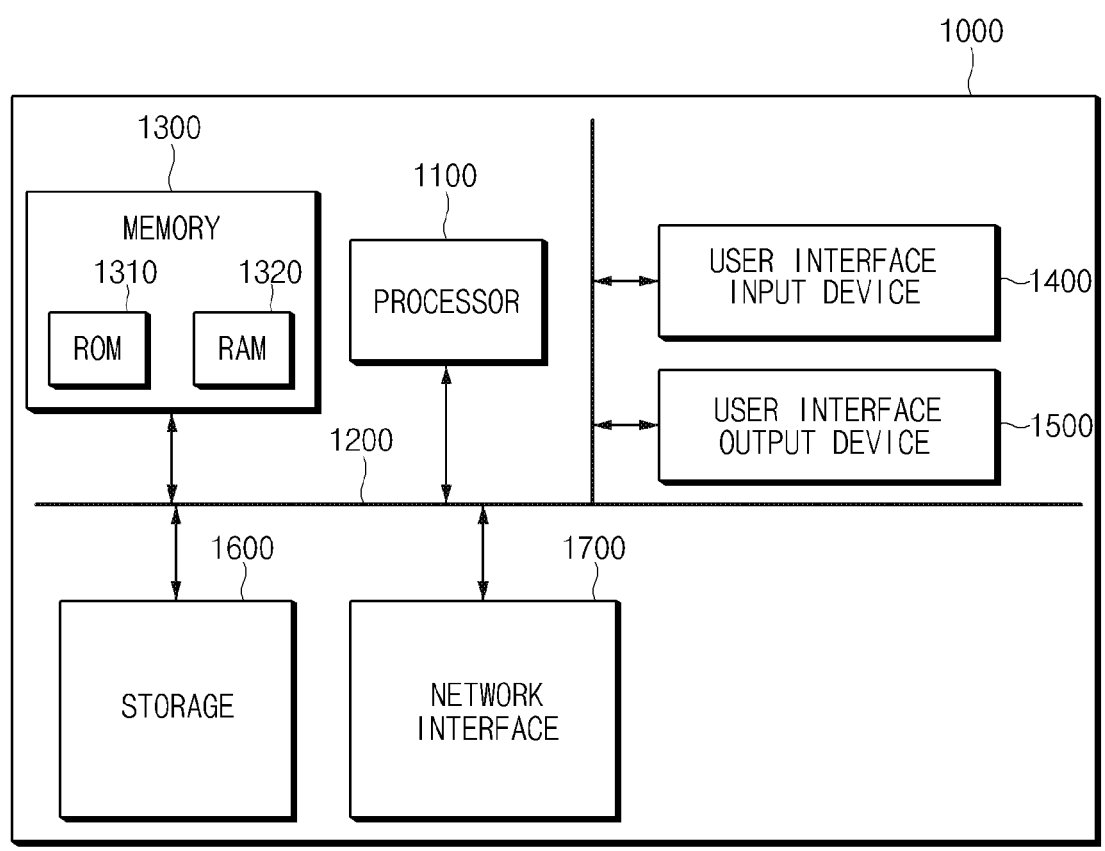
FIG. 7 is a diagram illustrating a configuration of a computing system executing a method according to an embodiment of the present disclosure.

FIG. 7 is a diagram illustrating a configuration of a computing system executing a method according to an embodiment of the present disclosure.

Referring to FIG. 7, a computing system 1000 may include at least one processor 1100, a memory 1300, a user interface input device 1400, a user interface output device 1500, storage 1600, and a network interface 1700, which are connected with each other via a bus 1200.

The processor 1100 may be a central processing unit (CPU) or a semiconductor device that processes instructions stored in the memory 1300 and/or the storage 1600. The memory 1300 and the storage 1600 may include various types of volatile or non-volatile storage media. For example, the memory 1300 may include a ROM (Read Only Memory) 1310 and a RAM (Random Access Memory) 1320.

Thus, the operations of the method or the algorithm described in connection with the embodiments disclosed herein may be embodied directly in hardware or a software module executed by the processor 1100, or in a combination thereof. The software module may reside on a storage medium (that is, the memory 1300 and/or the storage 1600) such as a RAM, a flash memory, a ROM, an EPROM, an EEPROM, a register, a hard disk, a removable disk, a CD-ROM. The exemplary storage medium may be coupled to the processor 1100, and the processor 1100 may read information out of the storage medium and may record information in the storage medium. Alternatively, the storage medium may be integrated with the processor 1100. The processor 1100 and the storage medium may reside in an application specific integrated circuit (ASIC). The ASIC may reside within a user terminal. In another case, the processor 1100 and the storage medium may reside in the user terminal as separate components.

In the apparatus for detecting the alcohol component and the method thereof according to an embodiment of the present disclosure, the driver's breath is distinguished from the passenger's breath and the influence of the passenger is removed to detect the alcohol component in the driver's breath, thereby accurately determining the driver's drinking state.

Hereinabove, although the present disclosure has been described with reference to exemplary embodiments and the accompanying drawings, the present disclosure is not limited thereto, but may be variously modified and altered by those skilled in the art to which the present disclosure pertains without departing from the spirit and scope of the present disclosure claimed in the following claims.

Therefore, the exemplary embodiments of the present disclosure are provided to explain the spirit and scope of the present disclosure, but not to limit them, so that the spirit and scope of the present disclosure is not limited by the embodiments. The scope of the present disclosure should be construed on the basis of the accompanying claims, and all the technical ideas within the scope equivalent to the claims should be included in the scope of the present disclosure.

What is claimed is:

1. An apparatus for detecting an alcohol component of a driver's breath, the apparatus comprising:
    a first inlet configured to absorb a driver's exhalation and a second inlet configured to absorb a passenger's exhalation, respectively;
    a sensor configured to detect an alcohol component in at least one of the driver's exhalation or the passenger's exhalation;
    a driver valve controlled to be opened or closed to allow the driver's exhalation to be introduced into the sensor, and a passenger valve controlled to be opened or closed to allow the passenger's exhalation to be introduced into the sensor; and
    a controller configured to determine whether a passenger is on board a vehicle and control the driver valve and the passenger valve to be open or closed based on a determination result.

2. The apparatus of claim 1, wherein the controller controls the driver valve and the passenger valve to be opened or closed to allow the driver's exhalation and the passenger's exhalation to be alternately introduced into the sensor when it is determined that the passenger is on board the vehicle based on the determination result.

3. The apparatus of claim 2, wherein the controller controls the driver valve to be opened and controls the passenger valve to be closed for a predetermined first time, to introduce the driver's exhalation into the sensor when the passenger is on board the vehicle, and then the controller controls the driver valve to be closed and controls the passenger valve to be opened for the first time, to introduce the passenger's exhalation into the sensor, thereby alternately introducing the driver's exhalation and the passenger's exhalation alternately into the sensor.

4. The apparatus of claim 3, wherein the controller determines whether either the driver's exhalation or the passenger's exhalation flowed into the sensor based on the predetermined first time.

5. The apparatus of claim 3, wherein, before starting the engine, the controller determines whether the alcohol component is detected in the driver's exhalation and the passenger's exhalation which are alternately introduced into the sensor and the controller determines the engine is capable of being started when the alcohol component is not detected in the driver's exhalation.

6. The apparatus of claim 5, wherein, after starting the engine, the controller determines whether the alcohol component is detected in the driver's exhalation and the passenger's exhalation alternately introduced into the sensor while driving and the controller determines the driving is maintained when the alcohol component is not detected in the driver's exhalation.

7. The apparatus of claim 5, wherein the controller determines whether the alcohol component is detected in the passenger's exhalation when the alcohol component is detected in the driver's exhalation while driving and the controller outputs a warning and controls to stop driving when the alcohol component is not detected in the passenger's exhalation.

8. The apparatus of claim 7, wherein the controller outputs a ventilation request message of a vehicle interior and controls to redetect the alcohol component in the driver's exhalation and the passenger's exhalation when the alcohol component is detected in the passenger's exhalation.

9. The apparatus of claim 1, wherein the controller controls the driver valve to be opened and controls the passenger valve to be closed, to introduce the driver's exhalation into the sensor and not to introduce the passenger's exhalation into the sensor when it is determined that the passenger is not on board the vehicle based on the determination result.

10. The apparatus of claim 1, wherein the driver valve and the passenger valve each include a solenoid valve, respectively.

11. A method of detecting an alcohol component of a driver's breath, the method comprising:
determining whether a passenger is on board a vehicle;
controlling a driver valve and a passenger valve to be opened or closed based on a determination result of the passenger's boarding; and
detecting an alcohol component in at least one of a driver's exhalation introduced into the sensor from a first inlet or a passenger's exhalation introduced into the sensor from a second inlet in response to opening or closing of the driver valve and the passenger valve.

12. The method of claim 11, wherein the driver valve and the passenger valve are controlled to be opened or closed when it is determined that the passenger is on board the vehicle based on the determination result, thereby allowing the driver's exhalation and the passenger's exhalation to alternately be introduced into the sensor.

13. The method of claim 12, wherein the driver valve is controlled to be opened and the passenger valve is controlled to be closed for a predetermined first time when the passenger is on board the vehicle, thereby allowing the driver's exhalation to be introduced into the sensor, and then the driver valve is controlled to be closed and the passenger valve is controlled to be opened for the predetermined first time, thereby allowing the passenger's exhalation to be introduced into the sensor, thereby allowing the driver's exhalation and the passenger's exhalation to alternately be introduced into the sensor.

14. The method of claim 13, wherein it is determined whether either the driver's exhalation or the passenger's exhalation is introduced into the sensor based on the preset first time.

15. The method of claim 13, wherein before starting the engine, it is determined whether the alcohol component is detected in the driver's exhalation and the passenger's exhalation alternately introduced into the sensor and it is determined the engine is capable of being started when the alcohol component is not detected in the driver's exhalation.

16. The method of claim 15, wherein after starting the engine, it is determined whether the alcohol component is detected in the driver's exhalation and the passenger's exhalation alternately introduced into the sensor while driving and it is controlled to maintain driving when the alcohol component is not detected in the driver's exhalation.

17. The method of claim 15, wherein it is determined whether the alcohol component is detected in the passenger's exhalation when the alcohol component is detected in the driver's exhalation while driving and a warning is output, and it is controlled to stop driving when the alcohol component is not detected in the passenger's exhalation.

18. The method of claim 17, wherein a vehicle interior ventilation request message is output and it is controlled to redetect the alcohol component in the driver's exhalation and the passenger's exhalation when the alcohol component is detected in the passenger's exhalation.

19. The method of claim 11, wherein the driver valve is controlled to be opened and the passenger valve is controlled to be closed when the passenger is not on board the vehicle based on the determination result, thereby allowing the driver's exhalation to be introduced into the sensor and to allow the passenger's exhalation not to be introduced into the sensor.

20. The method of claim 11, wherein the driver valve and the passenger valve each include a solenoid valve, respectively.

* * * * *